United States Patent [19]

Light et al.

[11] 4,411,830
[45] * Oct. 25, 1983

[54] BRIDGED TRICYCLIC ALCOHOL, PROCESS FOR PREPARING SAME AND PERFUMERY USE THEREOF

[75] Inventors: Kenneth K. Light, North Ogden, Utah; Joseph A. McGhie, Montclair, N.J.; Futoshi Fujioka, Wanamassa, N.J.; Takao Yoshida, West Long Branch, N.J.

[73] Assignee: International Flavors & Fragrances Inc., New York, N.Y.

[*] Notice: The portion of the term of this patent subsequent to Nov. 2, 1999, has been disclaimed.

[21] Appl. No.: 396,258

[22] Filed: Jul. 8, 1982

Related U.S. Application Data

[60] Division of Ser. No. 287,939, Jul. 29, 1981, Pat. No. 4,373,108, which is a continuation-in-part of Ser. No. 206,649, Nov. 13, 1980.

[51] Int. Cl.³ .......................... A61K 7/46; C11B 9/00
[52] U.S. Cl. ................................................ 252/522 R
[58] Field of Search ................................... 252/522 R

[56] References Cited

U.S. PATENT DOCUMENTS 4,301,302 11/1981 Sprecker et al. ........... 252/522 R X
4,357,360 11/1982 Light et al. ................. 252/522 R X Primary Examiner—Helen M. S. Sneed
Attorney, Agent, or Firm—Arthur L. Liberman

[57] ABSTRACT

Described are the compounds covered by the generic structure:

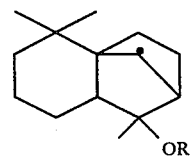

wherein "R" represents hydrogen or lithium.
The compound having the structure:

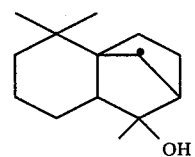

is useful in augmenting or enhancing the patchouli aroma of a perfume, cologne or perfumed article, such as a solid or liquid anionic, cationic, nonionic or zwitterionic detergent. The compound having the structure:

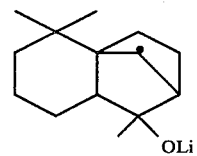

is an intermediate for preparing the compound having the structure:

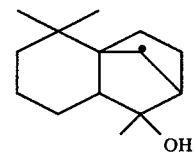

according to the process defined by the reaction:

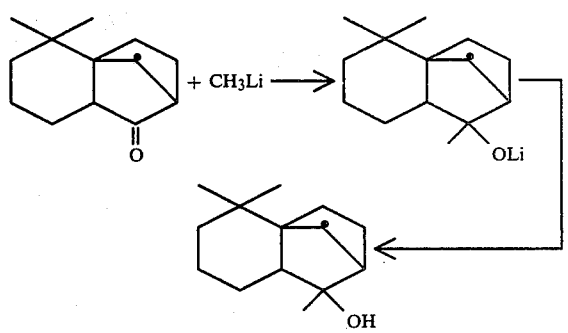
1 Claim, 2 Drawing Figures

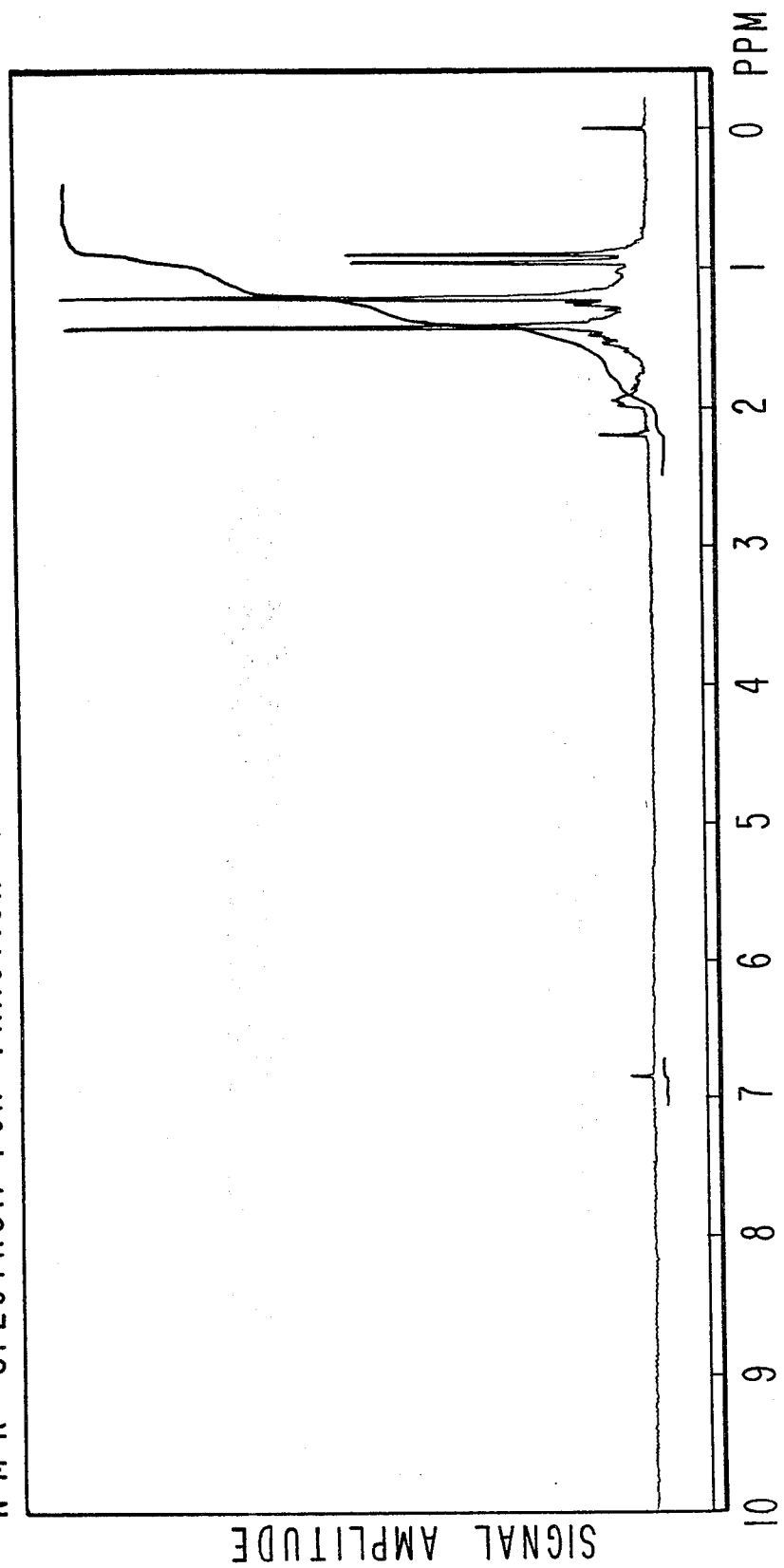
FIG.1 NMR SPECTRUM FOR FRACTION 4 OF EXAMPLE I.

IR SPECTRUM FOR FRACTION 4 OF EXAMPLE I.

BRIDGED TRICYCLIC ALCOHOL, PROCESS FOR PREPARING SAME AND PERFUMERY USE THEREOF

This is a divisional of application Ser. No. 287,939, filed July 29, 1981 now U.S. Pat. No. 4,373,108 which, in turn, is a continuation-in-part of application for U.S. Letters Patent Ser. No. 206,649 filed on Nov. 13, 1980.

BACKGROUND OF THE INVENTION

This invention relates to the compounds having the structure:

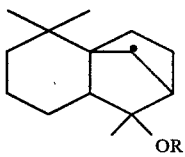

wherein "R" represents hydrogen or lithium with the compound having the structure:

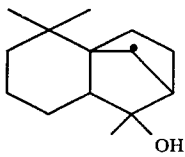

of this species useful in augmenting or enhancing the patchouli aroma of perfume compositions and perfumed articles and colognes and where the composition having the structure:

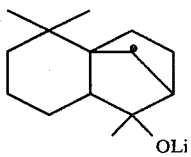

is used as an intermediate in preparing the compound having the structure:

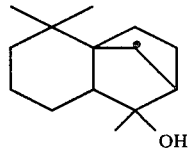

There has been considerable work performed relating to substances which can be used to impart (modify, augment or enhance) the fragrances to (or in) various consumable materials. These substances are used to diminish these natural materials, some of which may be in short supply and to provide more uniform properties in the finished product. Patchouli-like aromas are desirable in several types of perfume compositions, perfumed articles such as anionic, cationic, nonionic or zwitterionic detergents, cosmetic powders and drier added fabric softener articles, as well as colognes.

Tricyclic ketone compounds defined according to the generic structure:

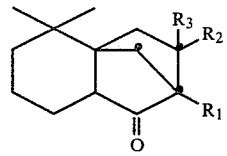

are shown to be useful in augmenting or enhancing woody, camphoraceous and ambery aromas in perfumes, perfumed articles and colognes. These tricyclic ketones are shown to be useful intermediates in preparing tricyclic alcohols defined according to application for U.S. Letters Patent Ser. No. 206,649 filed on Nov. 13, 1980.

The disclosure of said application for U.S. Letters Patent Ser. No. 206,649 filed on Nov. 13, 1980 is accordingly, and hereby incorporated into the instant case by reference.

BRIEF DESCRIPTION OF THE DRAWINGS

FIG. 1 is the NMR spectrum for fraction 4 of the distillation product of the reaction product produced according to Example I containing the compound having the structure:

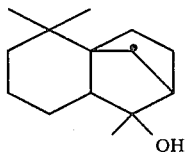

Figure 2:
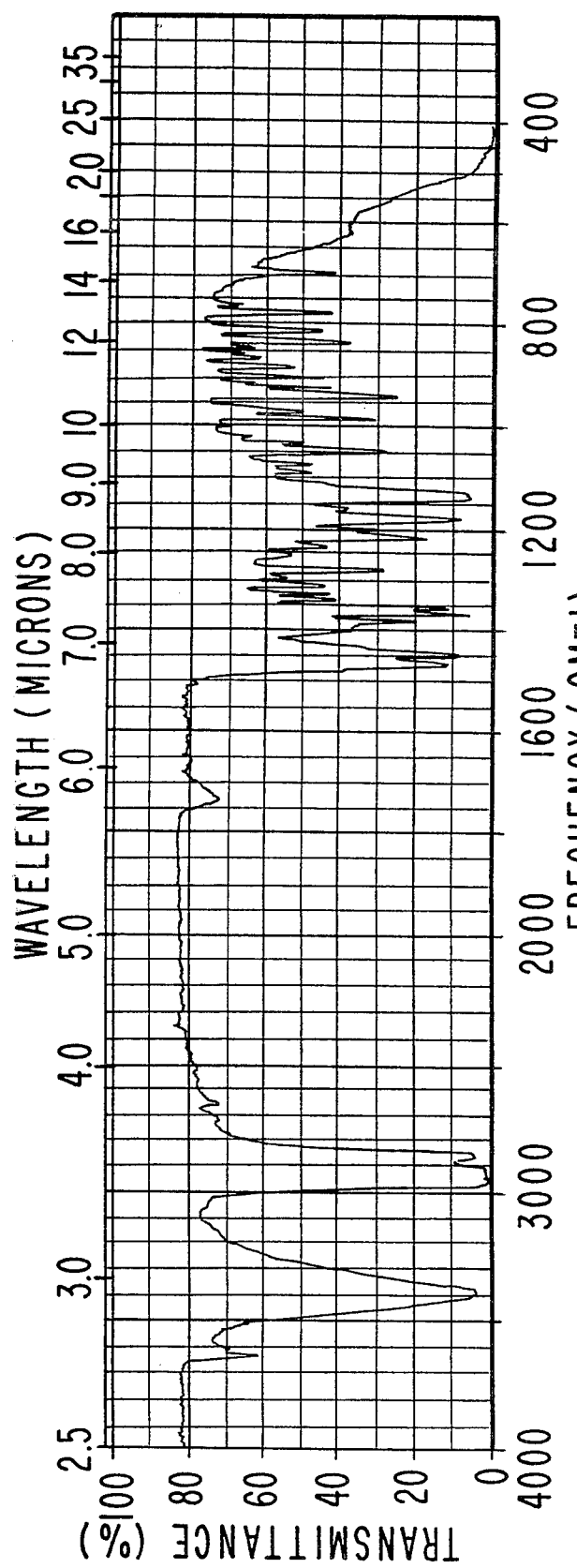

FIG. 2 is the infra-red spectrum for fraction 4 of the distillation product of the reaction product produced according to Example I containing the compound having the structure:

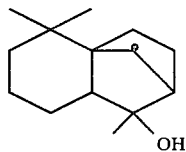

THE INVENTION

It has now been discovered that novel perfume compositions, colognes and perfumed articles (e.g., solid or liquid anionic, cationic and nonionic detergent compositions as well as dryer-added fabric softener articles and, in addition, cosmetic powders) having intense and pleasant patchouli aromas may be provided by the utilization of the tricyclic alcohol having the structure:

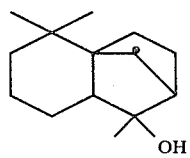

The compound having the structure:

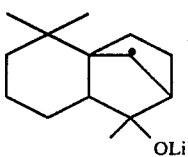

may be prepared by reacting the tricyclic ketone prepared according to any of Example I, II or III of U.S. Pat. No. 4,250,338 issued on Feb. 10, 1981 with methyl lithium or with methyl magnesium halide such as methyl magnesium bromide, methyl magnesium chloride or methyl magnesium iodide according to the processes described in detail, in application for U.S. Letters Patent Ser. No. 206,649 filed on Nov. 13, 1980, the specification for which is incorporated by reference herein.

Methyl lithium is, for example, first reacted with the tricyclic ketone of any of Examples I, II or III of U.S. Pat. No. 4,250,338 to form the lithium organometalic tricyclic compound having the structure:

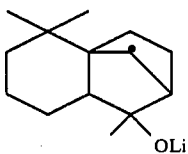

which is hydrolyzed in the presence of acid to form the product of of our invention having the structure:

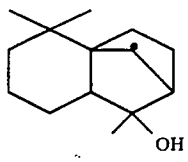

according to the reaction:

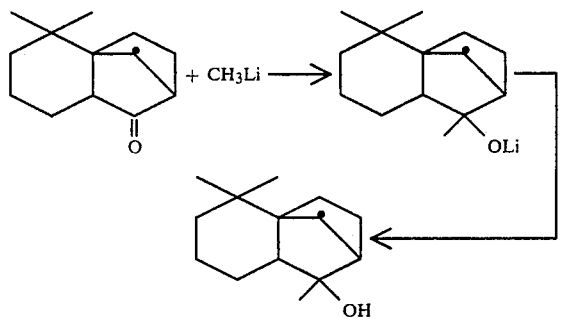

The tricyclic alcohol of our invention and one or more auxiliary perfume ingredients including e.g., other alcohols, aldehydes, ketones, terpenic hydrocarbons, nitriles, esters, lactones, natrual essential oils and synthetic essential oils may be admixed so that the combined odors of the individual components produce a pleasant and desired fragrance in the patchouli area. Such prefume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect to the perfume composition will be at least the sum total of the effects of each of the ingredients. Thus, the tricyclic alcohol of our invention can be used to alter, modify or enhance the aroma characteristics of a perfume composition, for example, by utilizing or moderating the olfactory reaction contributed by another ingredient in the composition.

The amount of tricyclic alcohol of our invention which will be effective in perfume compositions as well as in perfumed articles and colognes depends on many factors, including the other ingredients, their amounts and the effects which are desired. It has been found that perfume compositions containing as little as 0.01% of the tricyclic alcohol or even less (e.g., 0.005%) can be used to impart a patchouli aroma to soaps, cosmetics, detergents, powders and colognes. The amount employed can range up to 70% of the fragrance components and will depend on considerations of costs, nature of the end product, the effect desired on the finished product and the particular fragrance sought.

The tricyclic alcohol of our invention is useful (taken alone or together with other ingredients in perfume compositions) as (an) olfactory component(s) in detergents and soaps, space odorants and deodorants, perfumes, colognes, toilet water, bath preparations such as lacquers, brilliantines, pomades and shampoos; cosmetic preparations, such as creams, deodorants, hand lotions and sun screens; powders, such as talcs, dusting powders, face powders and the like. When used as (an) olfactory component as little as 1% of the tricyclic alcohol will suffice to impart an intense patchouli aroma to various formulations. Although, generally, no more than 60% of the tricyclic alcohol based on the ultimate end product is required in the perfume composition, amounts of tricyclic alcohol(s) of up to 95% may be used in such perfume composition.

When used in perfumed articles such as anionic, cationic, nonionic and zwitterionic detergents, or dryer-added fabric softener articles, cosmetic powders or deodorant compositions from 0.1% up to 5.0% by weight of the tricyclic alcohol based on the overall perfumed article weight may be used in the perfumed articles to impart an intense parchouli-like aroma.

In addition, the perfume composition or fragrance composition of our invention can contain a vehicle or carrier for the tricyclic alcohol. The vehicle can be a liquid, such as a non-toxic alcohol, a non-toxic glycol, or the like. The carrier can also be an absorbent solid, such as a gum (e.g., gum arabic) or components for encapsulating the composition (such as gelatin as by coacervation).

The following examples serve to illustrate processes for producing the tricyclic alcohol of our invention and processes for utilizing said tricyclic alcohol for its organoleptic properties.

All parts and percentages given herein are by weight unless otherwise apecified.

EXAMPLE I

Preparation of Tricyclic Alcohol

Reaction:

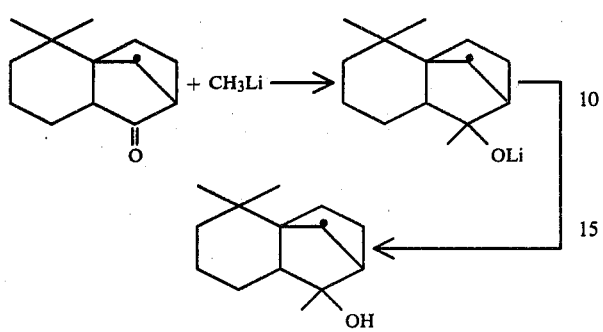

Into a 2000 cc reaction flask fitted with stirrer, condenser, thermometer and dropping funnel is placed a 1.8 molar solution of methyl lithium in anhydrous diethyl ether (833 cc; 1.50 moles methyl lithium). Under a nitrogen blanket, the methyl lithium solution is cooled to 10° C. and over a period of 45 minutes, dropwise, the tricyclic ketone produced according to Example I of U.S. Pat. No. 4,250,338 issued on Feb. 10, 1981 is added to the reaction mass. As to the addition as complete, the reaction mass is stirred and warmed up to room temperature (25° C.). An additional 0.3 moles of methyl lithium is added. The reaction mass is then hydrolyzed with an ammonium chloride solution. The resulting reaction product is separated into two layers, an organic layer and an aqueous layer. The organic layer is stripped of solvent and distilled yielding 204 grams of a crude product. Redistillation yields 197 grams (95% of theory).

The first distillation on a 12" Stone column yields the following fractions:

| Fraction No. | Vapor Temp. 0° C. | Liquid Temp. 0° C. | Vacuum mm. Hg. Pressure | Weight of Fraction |
|---|---|---|---|---|
| 1 | 100/105 | 120/70 | 1.5/1.5 | 14.0 |
| 2 | 110 | 120 | 1.5 | 17.0 |
| 3 | 110 | 120 | 1.5 | 24.0 |
| 4 | 110 | 120 | 1.5 | 43.0 |
| 5 | 110 | 129 | 1.5 | 43.0 |
| 6 | 110 | 195 | 1.5 | 18.0 |

The second distillation of a 12" Stone-packed column yields the following fractions:

| Fraction No. | Vapor Temp 0° C. | Liquid Temp. 0° C. | Vacuum mm. Hg. Pressure | Weight of Fraction |
|---|---|---|---|---|
| 1 | 125/130 | 125/135 | 4.5 | — |
| 2 | 130 | 135 | 2.0 | — |
| 3 | 130 | 135 | 2.0 | — |
| 4 | 130 | 140 | 2.0 | — |
| 5 | 130 | 198 | 2.0 | — |
| 6 | 130 | 198 | 2.0 | — |

FIG. 1 is the NMR spectrum for fraction 4 of the distillation product.

FIG. 2 is the infra-red spectrum for fraction 4 of the distillation product. Each of the spectra confirm that the structure of the reaction product in fraction 4 is:

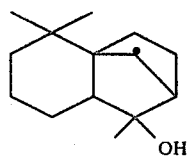

EXAMPLE II

Perfume Compositions

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petitgrain SA | 20 |
| Bergamot Oil | 30 |
| Alpha Methyl Ionone | 25 |
| Mixture of isomers of 1',2',3',4', 5',6',7',8'-octahydro-2',3',8',8'-tetramethyl-2'-acetonaphthones produced by the process of Example II (prior to GLC separation) of U.S. Pat. No. 3,911,018 issued on October 7, 1975 | 10 |
| Cyclized Bicyclo C-12 material produced according to the process of Example IV of Canadian Patent 854,225 issued October 20, 1970 | 5 |
| Iso Bornyl Cyclohexyl Alcohol | 10 |
| Benzyl Acetate | 25 |
| 2-n-Heptyl Cyclopentanone | 5 |
| Tricyclic Alcohol prepared according to Example I | 12.5 |
| TOTAL | 366.0 |

The foregoing blend is evaluated and found to have a high degree of richness and persistence in its novel patchouli character. It has excellent unique earthy/-patchouli notes contributed by the product produced according to Example I. This base composition can be admixed with aqueous ethanol, chilled and filtered to produce a finished cologne. The cologne so prepared has an excellent patchouli aroma. The base composition can also be used to scent soap or other toilet goods such as lotion, aerosols, sprays and the like.

EXAMPLE III

Preparation of a Cosmetic Powder

A cosmetic powder is prepared by mixing in a ball mill, 100 grams according to Example I. The resulting material has an excellent patchouli aroma.

EXAMPLE IV

Perfumed Liquid Detergent

Concentrated liquid detergents with patchouli aromas (which detergents are produced from the Lysine salt of n-dodecyl benzene sulfonic acid, as more specifically described in U.S. Pat. No. 3,948,818, issued on Apr. 6, 1976) are prepared containing the tricyclic alcohol of Example I and the perfumed composition of Example II. They are prepared by adding and homogenously mixing the appropriate quantity of tricycic alcohol derivative or perfume composition containing same in the liquid detergent. The detergents all possess excellent patchouli aromas.

EXAMPLE V

Preparation of a Cologne and Handkerchief Perfume

Perfume compositions and the tricyclic alcohol derivative of Example I are incorporated into colognes at concentrations of 1.5%, 2.0%, 2.5%, 3.0%, 3.5%, 4.0% and 5.0% in 80%, 85%, 90%, and 95% aqueous food grade ethanol; and into handkerchief perfumes at concentrations of 10%, 15%, 20%, 30%, 40% and 50% (in 85%, 90% and 95% aqueous food grade ethanol). Distinct and definitive patchouli aromas are imparted to the colognes and the the handkerchief perfumes.

EXAMPLE VI

Preparation of Soap Composition

One hundred grams of soap chips (obtained from Ivory® Soap) (a trademark of Proctor & Gamble Company of Cincinnati, Ohio) are mixed with two grams of each of the materials; the perfume compositions of Example II and the tricyclic alcohol of Example I until a substantially homogeneous composition is obtained. The resulting composition is melted at 180° C. for a period of 4 hours under 8 atmospheres nitrogen pressure. The resulting melt is cooled and formed into a soap bar. Each of the soap bars has an excellent patchouli aroma.

EXAMPLE VII

Preparation of a Liquid Detergent

Concentrated liquid detergents with patchouli aromas containing 0.2%, 0.5% and 1.2% of the perfume composition of Example II or the tricyclic alcohol of Example I are prepared by adding the appropriate quantity of the composition of Example II or the tricyclic alcohol of Example I to a liquid detergent known as P-87. The aromas of the liquid detergent increase with increasing concentration of composition but are all excellent patchouli aromas.

EXAMPLE XVIII

Utilizing the procedure of Example I of column 15 of U.S. Pat. No. 3,632,396, a nonwoven cloth substrate useful as a dryer-added fabric softening article of manufacture is prepared wherein the substrate, the substrate coating and the outer coating and the perfuming material are as follows:
1. a water "dissolvable" paper ("Dissolvo Paper"):
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of either the perfume composition of Example II or the tricyclic alcohol of Example I having patchouli aromas.

Fabric-softening compositions prepared as set forth above having the above patchouli aroma characterisitcs essentially consist of a substrate having a weight of about 3 grams per 100 square inches, a substrate coating of about 1.85 grams per 100 square inches of substrate and an outer coating of about 1.4 grams per 100 square inches of substrate, thereby providing a total patchouli-aromatized substrate and outer coating weight ratio of about 1:1 by weight of the substrate. The patchouli aromas are imparted in a pleasant manner to the head space in the dryer on operation thereof using the said dryer added fabric softening nonwoven fabric.

EXAMPLE IX

Granular Detergent

Granular detergent compositions prepared according to United Kingdom Patent Specification No. 1,501,498 having the following formula are prepared by spray-drying the following mixture as indicated below:

| Ingredient | COMPOSITION BY % BY WEIGHT | | | |
|---|---|---|---|---|
| | Example IX$^A$ | Example IX$^B$ | Example IX$^C$ | Example IX$^D$ |
| Sodium salt of ethoxylated fatty alcohol sulfate having an average of about 2.25 moles of ethylene oxide per mole of fatty alcohol[1] | 14.1 | 14.1 | 14.1 | 14.1 |
| Sodium tallow alkyl sulfate | 2.4 | 2.4 | 2.4 | 2.4 |
| Sodium silicate solids ratio: $SiO_2/Na_2O = 2.0$ | 0.0 | 2.0 | 6.0 | 0.0 |
| Sodium silicate solids ratio: $SiO_2/Na_2O = 3.2$ | 1.0 | 0.0 | 0.0 | 6.0 |
| Sodium tripolyphosphate | 24.0 | 24.0 | 24.0 | 24.0 |

| Ingredient | Example XIX$^A$ | Example XIX$^B$ | Example XIX$^C$ | Example XIX$^D$ |
|---|---|---|---|---|
| $Na_{12}(AlO_2,SiO_2)_{12} \cdot 27H_2O$[2] | 18.0 | 18.0 | 18.0 | 18.0 |
| Moisture | 10.0 | 10.1 | 9.9 | 10.2 |
| Sodium Sulfate | 25.0 | 25.0 | 20.0 | 20.0 |
| Minor ingredients including sodium toluene sulfonate, trisodium sulfosuccinate, dyes, brighteners | 4.0 | 2.4 | 3.6 | 2.3 |
| The tricyclic alcohol prepared according to Example I | 2.5 | 2.5 | 2.5 | 2.5 |

[1] Fatty alcohol composition 66% $C_{14}$; 33% $C_{16}$; 1% $C_{18}$
[2] Prepared as described in United Kingdom Patent 1,501,498; average particle size diameter 2 microns.

Laundry solutions containing the above detergent compositions are used to launder fabrics. Each of the laundry compositions both prior to and on laundering gives rise to a pleasant patchouli aroma.

What is claimed is:
1. A process for augmenting or enhancing the aroma of a perfume composition, cologne or perfumed article comprising the step of adding to a perfume base, a cologne base or a perfumed artilce base an aroma augmenting or enhancing quantity of the compound having the structure:

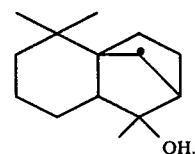

* * * * *